United States Patent [19]

Thizy et al.

[11] 4,119,724

[45] Oct. 10, 1978

[54] FUNGICIDAL COMPOSITIONS CONTAINING PHOSPHOROUS ACID AND DERIVATIVES THEREOF

[75] Inventors: André Thizy; Daniel Pillon; Jean-Claude Debourge; Guy Bernard Lacroix, all Lyon, France

[73] Assignee: Pepro, France

[21] Appl. No.: 787,154

[22] Filed: Apr. 13, 1977

Related U.S. Application Data

[62] Division of Ser. No. 527,380, Nov. 26, 1974, Pat. No. 4,075,324.

[30] Foreign Application Priority Data

Nov. 26, 1973 [FR] France ............................. 73.43081
Sep. 27, 1974 [FR] France ............................. 74.33409

[51] Int. Cl.$^2$ ........................... A61L 9/04; A01N 9/36
[52] U.S. Cl. ..................................... 424/45; 424/199; 424/200
[58] Field of Search ........................ 424/199, 200, 45

[56] References Cited

U.S. PATENT DOCUMENTS

| 2,507,468 | 5/1950 | Goggin | 424/199 |
| 2,773,796 | 12/1956 | Hackman et al. | 424/128 |
| 3,308,161 | 3/1967 | Shen | 424/200 |

FOREIGN PATENT DOCUMENTS 2,453,401  5/1975  Fed. Rep. of Germany.

Primary Examiner—Albert T. Meyers
Assistant Examiner—D. W. Robinson
Attorney, Agent, or Firm—Robert E. Burns; Emmanuel J. Lobato; Bruce L. Adams

[57] ABSTRACT

Fungicidal compositions containing phosphorous acid, inorganic and organic salts thereof are disclosed, as well as a method of controlling fungus disease in plants by applying such compositions.

16 Claims, No Drawings

FUNGICIDAL COMPOSITIONS CONTAINING PHOSPHOROUS ACID AND DERIVATIVES THEREOF

This is a divisional of application Ser. No. 527,380, filed Nov. 26, 1974 now U.S. Pat. No. 4,075,324.

BACKGROUND OF THE INVENTION

This invention relates to fungicidal compositions, which when applied to plants provide phosphorous acid, and concerns compositions based on phosphorous acid or its salts, and the method of applying the compositions to plants to control fungus disease.

More particularly, the invention relates to compositions and their use in controlling parasitic fungi in plants which contain as active material at least one compound from the group comprising phosphorous acid and its mineral or organic, mono acid, diacid or neutral, optionally hydrated, salts.

Organic phosphorus compounds with fungicidal properties have already been proposed. In particular, certain amino-alkyl phosphites have been described as having an interesting effect upon vine mildew. More recently, certain alkyl phosphates have been found to be active with respect to piriculariosis.

SUMMARY OF THE INVENTION

It has been discovered that the application to a plant of a compound which provides the plant with phosphorous acid, i.e. a compound which when applied yields a phosphite ion immediately or upon absorption is highly effective to control fungus diseases.

The fungicidal compositions of the invention contain as active ingredient at least one compound which when applied to the plant provide phosphite ion thereto in an amount effective to control fungus disease.

Also according to the invention, compounds more simple than conventional compounds have been found to show outstanding fungicidal properties and may be used as active material in compositions for protecting plants against fungus disease.

According to one aspect of the invention, fungus diseases in plants are controlled by applying to the plant a fungicidal composition containing as active material at least one compound selected from the group consisting of phosphorous acid, inorganic salts thereof and organic salts thereof.

Fungicidal compositions of the invention contain a fungicidally effective amount of at least one compound selected from the group consisting of phosphorous acid, inorganic salts thereof and organic salts thereof.

DESCRIPTION OF THE INVENTION

Examples of phosphite salts suitable for controlling fungal disease in accordance with the present invention include inorganic or mineral salts, for example salts of alkali metals, such as sodium, lithium, potassium, and salts of ammonium; organic salts including in particular nitrogen containing compounds which can accept a proton from phosphorous acid, such as primary, secondary or tertiary, optionally substituted aliphatic, aromatic, alicyclic or heterocyclic amines or of other nitrogen-containing derivatives, including for example imidazoles, cyclohexylamines, anilines, and morpholines. The aromatic and heterocyclic nitrogen containing compounds may be substituted, preferably with up to three alkyl groups, each containing from 1-4 carbon atoms. The foregoing salts are generally readily soluble in water; substantially insoluble or completely insoluble salts, such as salts of alkaline earth metals, i.e. magnesium, calcium, barium, strontium or of heavier metals, i.e. copper, iron, nickel, cobalt, manganese, zinc and aluminum may also be used in accordance with the invention.

These compounds are known per se; phosphorous acid and disodium phosphite are commercial products which can be used as starting materials for producing other salts by conventional processes, such as more or less strong neutralization, double decomposition, etc.

The compounds tested and, in the case of those which were not commercially available, have been prepared are as follows:

(1) phosphorous acid $H_3PO_3$ — m.p. 74° C.

(2) acid sodium or monosodium phosphite $NaH_2PO_3$

This salt is prepared by adding an aqueous solution of one equivalent of phosphorous acid to an aqueous solution of one equivalent of soda up to pH 4. The liquid is evaporated until syrupy in consistency and then cooled. The hydrate $NaH_2PO_3.2\text{-}5\ H_2O$ crystallizes. It is purified by recrystallization from water.

(3) disodium phosphite or neutral sodium phosphite $Na_2HPO_3$

An aqueous solution of one equivalent of phosphorous acid is added to an aqueous solution of two equivalents of soda up to pH 9. The solution is then crystallized by evaporation. This product corresponds to the formula $Na_2HPO_3.H_2O$ which becomes deliquescent at 53° C. The hydrate loses its water at 140° C. giving the anhydrous phosphite $Na_2HPO_3$.

(4) acid potassium or monopotassium phosphite $KH_2PO_3$

This compound is obtained in the same way as compound 2, except that the soda is replaced by potash.

(5) neutral potassium phosphite $K_2HPO_3$

This compound is prepared in the same way as compound 3, except that the soda is replaced by potash. Deliquescent crystals are obtained.

(6) acid ammonium phosphite - m.p. 123° C.

(7) acid triethyl amine phosphite

This compound is prepared in the same way as compound 2 except that the soda is replaced by triethyl amine.

(8) acid monoethanolamine phosphite $H_2PO_3^{\ominus\ \oplus}H_3NCH_2\text{—}CH_2\text{—}OH$ This compound is prepared in the same way as compound 2 except that the soda is replaced by monoethanolamine.

| Analysis for $C_2H_{10}NO_4P$ | C % | H % | N % | P % |
| --- | --- | --- | --- | --- |
| Calculated | 16.78 | 6.99 | 9.79 | 21.68 |
| Found | 16.91 | 6.99 | 9.88 | 21.67 |

(9) acid calcium phosphite $Ca(H_2PO_3)_2.H_2O$

This compound is prepared in the same way as compound 2, except that the soda is replaced by calcium carbonate. The solution is evaporated in vacuo. The water-soluble crystalline mass loses its water of crystallisation at 150° C.

(10) neutral calcium phosphite $CaHPO_3.H_2O$

This salt is precipitated by the action of neutral ammonium phosphite on calcium chloride. A white crystalline powder losing its water of crystallisation at 200° to 300° C. is obtained.

(11) barium diacid phosphite BaH$_2$(PO$_3$H)$_2$

This compound is obtained by neutralising phosphorous acid with barium carbonate. The precipitate is filtered and then evaporated to dryness in vacuo. The product which is soluble in water decomposes at around 130° C.

(12) neutral barium phosphite BaHPO$_3$

This compound is prepared by adding one equivalent of disodium phosphite to one equivalent of an aqueous solution of barium chloride. The neutral phosphite is a salt substantially insoluble in water. Under the effect of heat, it loses one molecule of water between 150° and 200° C. The acid phosphite is reformed by hydrolysing the neutral phosphite in boiling water.

(13) neutral copper(II)phosphite CuHPO$_3$.2 H$_2$O

Cupric chloride is reacted with ammonium phosphite. The product obtained is a blue, flaky or crystalline material.

(14) neutral nickel (II)phosphite

Nickel(II)chloride is added to phosphorus trichloride partially hydrolysed with ammonia. A precipitate corresponding to the formula 2(NiHPO$_3$)H$_2$O.6 H$_2$O. The product obtained is green in colour and loses about 3 molecules of water in the presence of sulphuric acid. At 250° C., it gives the compound 2(NiHPO$_3$).H$_2$O.

(15) trivalent iron phosphite Fe$_2$(HPO$_3$)$_3$

This compound is obtained by adding ferric chloride to phosphorous acid.

(16) manganous phosphite MnHPO$_3$.H$_2$O

Phosphorous acid is reacted with manganese(II)carbonate.

| Analysis for MnH$_3$PO$_4$ | H % | P % | Mn % |
|---|---|---|---|
| Calculated | 1.96 | 20.25 | 35.95 |
| Found | 1.21 | 20.17 | 36.05 |

(17) neutral zinc(II)phosphite ZnHPO$_3$

This compound is obtained by reacting ammonium phosphite with zinc sulphate or by dissolving zinc oxide in phosphorous acid. A compound corresponding to the formula ZnHPO$_3$.1.5 H$_2$O is obtained. It loses one molecule of water at 120° C. and the rest of its water at 280° C.

(18) neutral magnesium phosphite MgHPO$_3$.6 H$_2$O

This salt is precipitated by the action of one mol of neutral ammonium phosphite on one equivalent of magnesium chloride. After filtration, the salt is obtained in a yield of 68%. m.p. above 300° C.

| Centesimal analysis for MgHPO$_3$ | | | |
|---|---|---|---|
| % | H | Mg | P |
| Calculated | 6.14 | 11.30 | 14.60 |
| Found | 6.08 | 11.39 | 14.54 |

(19) neutral aluminium phosphite Al$_2$(HPO$_3$)$_3$

This salt is precipitated by the action of neutral ammonium phosphite on aluminium nitrates. A white precipitate is obtained and is filtered.

(20) cuprous phosphite Cu$_2$HPO$_3$.2 H$_2$O 16.4 g (0.2 mol) of phosphorous acid are mixed with one equivalent of cuprous oxide. The mixture is left to react for 1 hour. It undergoes spontaneous heating and changes colour from red to brown. The precipitate is filtered and the cuprous phosphite obtained in a yield of 97%.

| Centesimal analysis for Cu$_2$HPO$_3$.2 H$_2$O | | | |
|---|---|---|---|
| % | Cu | H | P |
| Calculated | 52.20 | 2.06 | 12.80 |
| Found | 53.35 | 2.06 | 12.84 |

(21) acid phosphite of 1,3-imidazole 16.4 g (0.2 mol) of phosphorous acid are dissolved in 30 ml of water. 13.6 g (0.2 mol) of 1,3-imidazole are then added dropwise with stirring and cooling. This salt is soluble in water: a precipitate is obtained by concentration followed by evaporation. Yield 83%, m.p. 113° C.

| Centesimal analysis for C$_3$H$_7$N$_2$O$_3$P | | | | |
|---|---|---|---|---|
| % | C | H | N | P |
| Calculated | 24.00 | 4.67 | 18.67 | 20.67 |
| Found | 24.06 | 4.75 | 18.78 | 20.68 |

(22) to (27) phosphites of organic bases

The procedure is as in the preceding Example, except that the imidazole is replaced successively by cyclohexyl amine, aniline, anilines substituted on the nucleus, in particular by 1 to 3 C$_1$-C$_4$-alkyl radicals, and morpholine. If the salt obtained is insoluble in water, the crude precipitate is filtered and then recrystallised from water.

The formulae, physical constants (melting point, solubility in water), yield and centesimal analysis are given in the following Table:

| Compound No. | Formula | Physical constants | Yield | % | Calc. | Found |
|---|---|---|---|---|---|---|
| 22 | C$_6$H$_5$-NH$_3^{\oplus}$ O$^{\ominus}$-P(=O)(H)-OH | m.p: 181° C insoluble | 81% | C<br>H<br>N<br>P | 41.14<br>5.71<br>8.00<br>17.71 | 41.00<br>6.03<br>8.06<br>17.66 |
| 23 | cyclohexyl-NH$_3^{\oplus}$ O$^{\ominus}$-P(=O)(H)-OH | m.p.: 207° C insoluble | 91% | C<br>H<br>N<br>P | 39.78<br>8.84<br>7.73<br>17.13 | 39.56<br>9.04<br>7.79<br>17.06 |
| 24 | 2,4,6-trimethylphenyl-NH$_3^{\oplus}$ O$^{\ominus}$-P(=O)(H)-OH | m.p: 165.5° C insoluble | 70% | C<br>H<br>N<br>P | 49.77<br>7.37<br>6.45<br>14.29 | 49.90<br>7.40<br>6.44<br>14.30 |

-continued

| Compound No. | Formula | Physical constants | Yield | Analysis % | Calc. | Found |
|---|---|---|---|---|---|---|
| 25 | (cyclohexyl-NH₂)⁺ ⁻O—P(=O)(H)—OH | m.p: 77° C insoluble | 41% | C<br>H<br>N<br>P | 28.40<br>7.10<br>8.28<br>18.34 | 28.36<br>7.12<br>8.29<br>18.34 |
| 26 | IsoC₃H₇—C₆H₄—NH₂⁺ ⁻O—P(=O)(H)—OH | m.p: 168° C insoluble | 93% | C<br>H<br>N<br>P | 49.77<br>7.37<br>6.45<br>14.29 | 49.94<br>7.40<br>6.37<br>14.34 |
| 27 | (2-isoC₃H₇-C₆H₄)—NH₃⁺ ⁻O—P(H)(=O)—OH | insoluble m.p: = 148.3° C | 87% | C<br>H<br>N<br>P | 49.77<br>7.37<br>6.45<br>14.29 | 49.98<br>7.32<br>6.41<br>14.30 |

The fungicidal properties of the compounds according to the invention are various, but are particularly interesting in the case of vine mildew, as the following Examples show:

EXAMPLE 1

In vitro Test on Mycelian Growth

The compounds according to the invention are studied for their effect on the mycelian growth of the following fungi:

*Rhizoctonia solani,* responsible for neck canker
*Botrytis cinerea,* responsible for grey rot
*Piricularia oryzae,* responsible for piriculariosis in rice.

The "Agar Plate dilution" method is used for each test. A mixture of gelose and an acetone solution or a wettable powder containing the material to be tested in a concentration of 0.25 g/l is poured into a Petri dish at a temperature of approximately 50° C.

The wettable powder is prepared by mixing the following ingredients for 1 minute in a cutting mill:

| | |
|---|---|
| active material to be tested | 20 % |
| deflocculant (calcium lignosulphate) | 5 % |
| wetting agent (sodium alkylaryl sulphonate) | 1 % |
| filler (aluminium silicate) | 74 % |

This wettable powder is then mixed with water in a quantity sufficient for application in the required dose.

The gelose-containing mixture is then allowed to solidify, after which mycelian culture discs of the fungus are placed on it.

A Petri dish similar to the preceding Petri dish, except that the gelose-containing medium does not contain any active material, is used as control.

After 4 days at 20° C., the surface area of the inhibition zone observed is evaluated and expressed as a percentage of the inoculated surface area.

Under these conditions, it is found that compound 8 produces 51 and 60% inhibition of *Pythium de Baryanum* and *Rhizoctania solani*, respectively, and that compound 14 produces 48, 59 and 78% inhibition of *Botrytis cinerea, Piricularia oryzae* and *Rhizoctonia solani*, respectively.

EXAMPLE 2

In vivo Test on *Plasmopara viticola* in Vine Plants (a) Preventive Treatment The leaves of pot-grown vine plants (Gamay variety) are sprayed underneath using a spray gun with an aqueous suspension of a wettable powder having the following composition (by weight):

| | |
|---|---|
| active material to be tested | 20 % |
| deflocculant (calcium lignosulphate) | 5 % |
| wetting agent (sodium alkylaryl sulphonate) | 1 % |
| filler (aluminium silicate) | 74 % | in the required dilution containing the active material to be tested in the required dose. Each test was repeated three times.

After 48 hours, the plants are contaminated by spraying the leaves underneath with an aqueous suspension of approximately 80,000 units/cc of spores of the fungus.

The pots are then placed in an incubation cell at 20° C./100% relative humidity for a period of 48 hours.

The plants are inspected 9 days after infestation.

Under these conditions, it is found that, in a dose of 0.5 g/l, compounds 1 to 8, 10, 12, 13, 14, 16, 17, 19, 20 and 24 afford total protection, whilst compounds 15, 18, 21, 22, 25, 26, 27 afford good protection.

In addition, it was found that none of the compounds tested showed the least phytotoxicity.

(b) Treatment after Contamination

The procedure is as described in (a) above, except that the plants are first of all contaminated and then treated with the active material to be tested, the plants being inspected 9 days after contamination.

Under these conditions, it is found that, in a dose of 1 g/l, compounds 1 to 8, 14, 16, 17, 21, 22, 24, 25 and 26, completely stop the development of mildew on the vine plants.

(c) Systemic Test by Root Absorption on Vine Mildew

Several vine stocks (Gamay variety) each accommodated in a pot containing vermiculite and a nutritive solution are sprinkled with a solution containing 0.5 g/l of the material to be tested. After 2 days, the vine is contaminated with an aqueous suspension containing 100,000 spores/cc of *Plasmopara viticola*. The spores are then left to incubate for 48 hours in a room at 20° C./100% relative humidity. The degree of infestation is assessed after about 9 days in relation to an infested control which has been sprinkled with 40 cc of distilled water.

Under these conditions, it is found that, in this dose of 0.5 g/l, compounds 1 to 8, 12, 17, 19, 21, 22, 25, absorbed by the roots afford total protection, whilst compounds 10, 13 and 23 afford good protection to the vine leaves against mildew, which demonstrates clearly the systemic nature of these compounds.

(d) Open-air Test

Groups of vine stocks (Gamay variety) are treated on the 27th June, 4th, 11th and 18th July, 1st and 7th August, with a spray of wettable powder containing 50% of an active material, namely compound 13 and manganese ethylene-1,2-bis-dithiocarbamate or manebe.

The following Table shows the results of inspections made approximately 1 month, 2 months and 2.5 months after the last treatment. It should be noted that, in August and September, the mildew Plasmopara viticola was extremely virulent on account of heavy rainfall. For a uniform dose of 2 g/l, the results are expressed as percentage protection in relation to a contaminated but untreated control.

| Compound | Inspection date | | |
|---|---|---|---|
| | 3/9 | 2/10 | 20/10 |
| No. 13 | 94 | 66 | 50 |
| Manebe | 96 | 62 | 15 |
| Control | 15 | 0 | 0 |

This Table clearly shows the remarkable persistence of the compound according to the invention. In addition, no evidence of phytotoxicity was found in any of the treated plants.

These Examples clearly demonstrate the remarkable fungicidal properties of the compounds according to the invention. Individually they are characterised by their immediate, persistent or systemic effect, in particular upon vine mildew.

Some of these compounds, more especially the water-soluble salts, show better systemic properties than the substantially insoluble salts. By contrast, the substantially insoluble salts are more persistent in their effect. It is for this reason that it is possible with advantage to mix these products with one another, more especially with a soluble compound and a less soluble compound so as to combine protection of seedlings with high persistence.

EXAMPLE 3

Avocado Test

Avocado seedlings (variety *Persea indica*) are planted in a soil infested with *Phytophtora cinnamomi*, after which the soil is sprayed with a solution containing 3 g/l of ammonium phosphite. Some seedlings are left untreated as controls. Under these conditions, it is found after 20 days that the roots of the controls are completely dead, whilst 90% of the treated seedlings are healthy.

EXAMPLE 4

Pineapple Test

Pineapple seedlings are contaminated with *Phytophtora parasitica* and then treated after 48 hours by spraying with a solution containing 0.5 g/l of calcium phosphite. After 30 days, the fungus is completely inhibited in the treated seedlings, whilst the controls are infested.

All these Examples clearly show the remarkable fungicidal activity of the compounds according to the invention, on the one hand a systemic anti-mildew activity which both prevents and stops the development of vine mildew, and on the other hand on certain phytophtora as well.

However, they have also been found to be extremely effective in controlling other types of parasitic fungi such as *Peronospora tabacci, Pseudoperonospora humili, Phytophtora cactorum, Phytophtora capsici, Bremia lactucae, Phytophtora infestans, Peronospora sp., Phytophtora palmivora, Phytophtora phaseoli, Phytophtora megasperma, Phytophtora drechsteri* and other *Phytophtora sp.*, in other temperate-climate or tropical-climate plants such as: tobacco, hop, market-gardening cultures, especially strawberry plants, green pepper, onion, sweet pepper, tomato, bean, and in ornamental plants, in pineapple, soya, citrus, cocoa, coconut palm, heavea rubber. Accordingly, the compounds according to the invention are particularly suitable for use in the preventive or curative treatment of fungus disease in plants, especially fungus disease caused by phycomycetes in the vegetables already mentioned, but also in other plants which can be attacked by these fungi.

The compounds according to the invention may be used with advantage in admixture with one another or with other known fungicides, such as metal dithiocarbamates (manebe, zinebe, mancozebe), basic salts or hydroxides of copper (oxychloride, oxysulphate), (tetrahydro)phthalimides (captane, captafol, folpel), N-(1-butyl carbamoyl)-2-benzimidazole, methyl carbamate (benomyl), 1,2-di-(3-methoxy or ethoxy)-carbonyl-2-thioureidobenzenes (thiophanates), methyl 2-benzimidazole carbamate, etc., either to complete the range of activity of the compounds according to the invention or to increase their persistence.

It has also been found that the compounds according to the invention may be mixed with other fungicidal, antimildew phosphorus derivatives, including the 2-hydroxy-1,3,2-dioxaphospholanes, the $\beta$-hydroxyethyl phosphites, the phosphonic monoesters and their salts, the phosphonic diesters, the cyclic diphosphorus compounds and the aminophosphites disclosed, respectively, in French patent applications Nos. 73 01803, 73 37994, which corresponds to U.S. application Ser. No. 432,492 and in French patent applications Nos. 73 45627, 71 08995, 74 10988 and 74 13246.

The doses in which the compounds according to the invention are used may vary within wide limits, depending both upon the virulence of the fungus and upon the climatic conditions. Doses of from 0.01 to 5 g/l of active material are generally suitable.

For their practical application, the compounds according to the invention are rarely used on their own. Instead they generally form part of formulations which, as a rule, contain a support and/or a surfactant in addition to the active material according to the invention.

In the context of the invention, a support is an organic or mineral, natural or synthetic material with which the active material is associated to facilitate its application to the plant, to seeds or to soil, or its transportation or handling. The support can be solid (clays, natural or synthetic silicates, resins, waxes, solid fertilizers) or fluid (water, alcohols, ketones, petroleum fractions, chlorinated hydrocarbons, liquefied gases).

The surfactant can be an ionic or non-ionic emulsifier, dispersant or wetting agent such as, for example, salts of polyacrylic acids and lignin-sulphonic acids, condensates of ethylene oxide with fatty alcohols, fatty acids or fatty amines.

The compositions according to the invention can be prepared in the form of wettable powders, soluble powders, dusting powders, granulates, solutions, emulsifiable concentrates, emulsions, suspended concentrates and aerosols.

The wettable powders according to the invention can be prepared in such a way that they contain from 20 to 95% by weight of the active material, and they normally contain, in addition to a solid support, from 0 to 5% by weight of a wetting agent, from 3 to 10% by weight of a dispersant and, when necessary, from 0 to 10% by weight of one or more stabilizers and/or other additives, such as penetration agents, adhesives or antilumping agents, colorants . . . etc.

One example of the composition of a wettable powder is given below:

| active material | 50 % |
|---|---|
| calcium lignosulphate (deflocculant) | 5 % |
| anionic wetting agent | 1 % |
| antilumping silica | 5 % |
| kaolin (filler) | 39 % |

Powders soluble in water are obtained by mixing from 20 to 95% by weight of active material, 0 to 10% of an antilumping agent with the remainder being a water soluble filler, mainly a salt. An example of the compositon of a soluble powder is the following:

| active material | 70 % |
|---|---|
| anionic wetting agent | 0.5 % |
| antilumping silica | 5 % |
| sodium sulfate (soluble filler) | 24.5 % |

Aqueous dispersions and emulsions, for example compositions obtained by diluting with water a wettable powder or an emulsifiable concentrate according to the invention, are included within the general scope of the invention. These emulsions can be of the water-in-oil type or of the oil-in-water type, and can have a thick consistency resembling that of a "mayonnaise".

The compositions according to the invention can contain other ingredients, for example protective colloids, adhesives or thickeners, thioxtropic agents, stabilizers or sequestrants, as well as other active materials known to have pesticidal properties, especially acaricides or insecticides.

The compounds thus defined may be applied to the plants to be protected by conventional methods of applying pesticides, such as spraying, scattering, powdering, soaking.

What we desire to claim and protect by Letters Patent is:

1. A method of controlling fungus disease in plants comprising applying to said plants in a fungicidally effective amount at least one salt of the formula

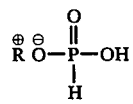

wherein R is triethyl amine, ethanol amine, 1,3-imidazole, cyclohexyl amine, aniline, aniline containing one to three alkyl substituents of 1 to 4 carbon atoms on the aromatic ring or morpholine.

2. A method according to claim 1 in which an aniline salt of phosphorous acid wherein said aniline is substituted on the aromatic ring with up to 3 alkyl groups, each alkyl group containing 1 to 4 carbon atoms is applied to said plant.

3. A method according to claim 1 in which R is triethyl amine or ethanol amine.

4. A method according to claim 1 in which R is 1,3-imidazole, cyclohexyl amine, aniline, aniline containing one to three alkyl substituents of 1 to 4 carbon atoms on the aromatic ring or morpholine.

5. A fungicidal composition for controlling fungus disease in plants comprising a fungicidal amount of at least one salt of the formula

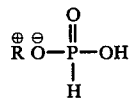

wherein R is triethyl amine, ethanol amine, 1,3-imidazole, cyclohexyl amine, aniline, aniline containing one to three alkyl substituents of 1 to 4 carbon atoms on the aromatic ring or morpholine, in admixture with an agriculturally acceptable carrier.

6. A fungicidal composition according to claim 5 in which said salt of phosphorous acid is an aniline salt, wherein said aniline is substituted on the aromatic ring with 1 to 3 alkyl groups of 1 to 4 carbon atoms.

7. A fungicidal composition according to claim 5 which also contains an agriculturally acceptable surfactant.

8. A fungicidal composition according to claim 5 in which said carrier is fluid and wherein said composition contains an agriculturally acceptable surfactant.

9. A fungicidal composition according to claim 8 in which said fluid is not toxic to plants and is selected from the group consisting of water alcohol, ketone, petroleum fraction, chlorinated hydrocarbon and liquified gas.

10. A composition according to claim 5 in which said carrier is solid and said composition is in powder form.

11. A fungicidal composition according to claim 5 in which said carrier is solid and said composition is in powder form and also contains an agriculturally acceptable surfactant.

12. A fungicidal composition according to claim 11 in which said carrier is a member selected from the group consisting of natural or synthetic silicate, resin, wax and solid fertilizer.

13. A fungicidal composition according to claim 5 in which said carrier is solid and said composition is in the form of a wettable powder and also contains an agriculturally acceptable surfactant.

14. A fungicidal composition according to claim 5 which contains from 20 to 95% by weight of said active material, from 0 to 5% by weight of a wetting agent from 3 to 10% by weight of a dispersant, and optionally containing from 0 to 10% by weight of at least one stabilizer, and also optionally containing solid support, penetration agent, adhesive, antilumping agent or colorant.

15. A fungicidal composition according to claim 5 in which R is triethyl amine or ethanol amine.

16. A fungicidal composition according to claim 5 in which R is 1, 3-imidazole, cyclohexyl amine, aniline, aniline containing one to three alkyl substituents of 1 to 4 carbon atoms on the aromatic ring or morpholine.

* * * * *